(12) United States Patent
Koike et al.

(10) Patent No.: US 7,658,538 B2
(45) Date of Patent: Feb. 9, 2010

(54) METHOD FOR EVALUATING SOLDER JOINT PORTION

(75) Inventors: Hirofumi Koike, Anjo (JP); Akikazu Matsumoto, Anjo (JP); Wataru Yagi, Nagoya (JP); Takefumi Isogai, Chiryu (JP); Yoshiharu Hirose, Aichi-gun (JP); Hiroaki Kadoura, Seto (JP); Juntaro Seki, Aichi-gun (JP); Hisaaki Takao, Seto (JP)

(73) Assignee: Aisin Seiki Kabushiki Kaisha, Kariya-shi (JP)

( * ) Notice: Subject to any disclaimer, the term of this patent is extended or adjusted under 35 U.S.C. 154(b) by 0 days.

(21) Appl. No.: 12/056,745

(22) Filed: Mar. 27, 2008

(65) Prior Publication Data

US 2008/0240201 A1 Oct. 2, 2008

(30) Foreign Application Priority Data

Mar. 30, 2007 (JP) ............................. 2007-093762

(51) Int. Cl.
*G01N 25/72* (2006.01)
(52) U.S. Cl. ......................................... 374/5
(58) Field of Classification Search ............... 374/5; 703/2
See application file for complete search history.

(56) References Cited

U.S. PATENT DOCUMENTS

2008/0015827 A1* 1/2008 Tryon et al. .................. 703/2

FOREIGN PATENT DOCUMENTS

| JP | 2004-85397 | 3/2004 |
|---|---|---|
| JP | 2004-119434 | 4/2004 |

* cited by examiner

*Primary Examiner*—Andre J Allen
(74) *Attorney, Agent, or Firm*—Oblon, Spivak, McClelland, Maier & Neustadt, L.L.P.

(57) ABSTRACT

A method for evaluating a solder joint portion by means of which a part and a substrate are joined to each other includes a preparation process for preparing the substrate including the solder joint portion, a thermal shock process for applying thermal shock to the solder joint portion multiple times, and an evaluation process for obtaining a change of a crystal grain size in the solder joint portion caused by the application of the thermal shock so as to evaluate a lifespan of the solder joint portion based on the change of the crystal grain size obtained.

13 Claims, 8 Drawing Sheets

FIG. 13

METHOD FOR EVALUATING SOLDER JOINT PORTION

CROSS REFERENCE TO RELATED APPLICATIONS

This application is based on and claims priority under 35 U.S.C. §119 to Japanese Patent Application No. 2007-093762, filed on Mar. 30, 2007, the entire content of which is incorporated herein by reference.

FIELD OF THE INVENTION

This invention generally relates to a method for evaluating a solder joint portion.

BACKGROUND

JP2004-119434A discloses a method for evaluating fatigue of Sn—Ag system solder joint portion. According to the evaluation method disclosed, the focus is on Sn phase and $Ag_3Sn$ phase that exists independently from the Sn phase. Then, a dimension d of the $Ag_3Sn$ phase and the Sn phase is measured. A phase growth evaluation parameter S is obtained by calculating the fourth power of the measured dimension d. The Sn phase and the $Ag_3Sn$ phase are enlarged while being exposed to thermal cycles and therefore the dimension d increases as a whole. A relationship between a thermal fatigue crack initiation cycle Ni corresponding to thermal cycles with which the fatigue crack is generated in the solder joint portion, and the phase growth evaluation parameter S is then determined. That is, the thermal fatigue crack initiation cycle Ni and a phase growth evaluation parameter Si at that time have a following relationship therebetween: $Si=A*Ni^\alpha$ wherein A and $\alpha$ are constants determined depending on a type of solder. A thermal fatigue life of the solder joint portion caused by application of the thermal cycles, i.e., a lifetime before the crack is initiated in the solder joint portion, is determined on the basis of a change rate $\Delta S$ of an increase of the phase growth evaluation parameter Si.

JP2004-85397A discloses a method for estimating a lifespan of a solder joint portion using a simulation model. According to the method disclosed, a simulation model in which a crack is not generated is prepared and used for obtaining inelastic strain occurring in the solder joint portion at a time temperature cycles are applied to the solder joint portion. Then, a crack initiation cycle is acquired on the basis of the inelastic strain obtained. On the basis of a relationship between a crack propagation speed obtained by a crack propagation test on solder material and a fracture mechanics parameter, and a relationship between the fracture mechanics parameter obtained by using the simulation model and a crack length, the crack propagation speed is obtained as a function of the crack length to thereby acquire a crack propagation lifespan that is a lifetime before the crack reaches a predetermined length.

However, according to the method for evaluating fatigue of a solder joint portion disclosed in JP2004-119434A, only the thermal fatigue crack initiation cycle is predicted, which may be insufficient for the prediction of the lifespan of the solder joint portion. In addition, the method for estimating a lifespan of a solder joint portion disclosed in JP2004-85397A does not include an actual test and thus durability is insufficient. In the related industry, it is desired to develop a method for evaluating a solder joint portion that can further effectively evaluate the lifespan of the solder joint portion.

A need thus exists for a method for evaluating a solder joint portion which is not susceptible to the drawback mentioned above.

SUMMARY OF THE INVENTION

According to an aspect of the present invention, a method for evaluating a solder joint portion by means of which a part and a substrate are joined to each other includes a preparation process for preparing the substrate including the solder joint portion, a thermal shock process for applying thermal shock to the solder joint portion multiple times, and an evaluation process for obtaining a change of a crystal grain size in the solder joint portion caused by the application of the thermal shock so as to evaluate a lifespan of the solder joint portion based on the change of the crystal grain size obtained.

BRIEF DESCRIPTION OF THE DRAWINGS

The foregoing and additional features and characteristics of the present invention will become more apparent from the following detailed description considered with reference to the accompanying drawings, wherein.

DETAILED DESCRIPTION

A method for evaluating a solder joint portion according to embodiments of the present invention includes a preparation process, a thermal shock process, and an evaluation process. The preparation process includes preparing a substrate equipped with a solder joint portion. The thermal shock process includes applying thermal shock to the solder joint portion multiple times. The evaluation process includes obtaining a change of crystal grain size (precisely, tin crystal grain size in a longitudinal diameter) in the solder joint portion caused by the application of the thermal shock so as to evaluate a lifespan of the solder joint portion based on the change of crystal grain size obtained. The substrate, which at least includes a solder joint portion, may be an electrical circuit board, an electronic circuit board, and the like. The solder joint portion is a joint portion including solder as a base material. In addition, the solder joint portion is a portion by means of which a part such as an electronic part and a substrate are joined to each other. The solder is a metal of which a melting point is lower than 427° C. The solder is composed of a tin (Sn) system, for example. The solder can contain at least one of antimony (Sb), silver (Ag), copper (Cn), bismuth (Bi), aluminum, indium (In), zinc (Zn), and the like as required. Thus, for example, Sn system, Sn—Ag system, Sn—Cn system, Sn—In system, Sn—Ag—Cn system, Sn—Zn system, or Sn—Pb system solder can be considered. In this case, however, in view of environmental concerns, the solder may desirably contain less lead (Pb) or substantially no lead. The solder constituting the solder joint portion contains tin as a main component, for example. That is, the solder contains tin equal to or greater than 60% in mass ratio. For example, the solder contains 0.5% to 10% silver, 0.1% to 5% copper in mass ratio, and the remainder including tin and inevitable impurities.

The thermal shock is generally achieved by an application of a temperature cycle to the solder joint portion. The temperature cycle includes operations for maintaining the solder joint portion to be in a low temperature atmosphere of less than 0° C. and in a high temperature atmosphere of greater than 0° C., two of which are alternately performed. For example, a temperature range between −60° C. and 0° C. (exclusive) is applicable to the low temperature atmosphere, which depends on types or intended uses of the solder joint portion. In addition, for example, a temperature range between 0° C. (exclusive) and 150° C. is applicable to the high temperature atmosphere, which depends on types or intended uses of the solder joint portion. The low temperature atmosphere is maintained for 5 to 200 minutes, for example, which depends on types or intended uses of the solder joint portion. In addition, the high temperature atmosphere is maintained for 5 to 200 minutes, for example, which depends on types or intended uses of the solder joint portion. The lifespan of the solder joint portion is evaluated on the basis of the change of crystal grain size in the solder joint portion caused by the application of the thermal shock. Precisely, the lifespan of the solder joint portion is based on a rate of crack growth or propagation in the solder joint portion.

The change of crystal grain size in the solder joint portion is based on, for example, an initial crystal grain size before the thermal shock is applied and a grain size after the thermal shock is applied multiple times. In such manner, the crack initiation in the solder joint portion is predicted to thereby evaluate the lifespan of the solder joint portion.

In the evaluation process, for example, it is determined that the lifespan of the solder joint portion is reaching its end when the crystal grains, each of which size is reduced because of the application of the thermal shock, increase. The reduction of the crystal grain size is assumed to affect the crack initiation in the solder joint portion. At this time, an area in the solder joint portion where the crystal grain size is first reduced is assumed to be a start point of the crack. This is because it is assumed that a strain stress concentration portion is formed at a portion where the crystal grain size is reduced in the solder joint portion.

In the evaluation process, a change in an existence ratio of crystal grains each having a predetermined size or more/less before and after the thermal shock process is obtained. Then, based on the obtained change, the lifespan of the solder joint portion is evaluated. In the cases where the change in the existence ratio of the crystal grains each having the predetermined size or more/less between before and after the thermal shock process is large, it is assumed that the lifespan of the solder joint portion is reaching its end as compared to a case where the change in the existence ratio of the crystal grains between before and after the thermal shock process is small. The predetermined size of the crystal grain used for the existence ratio is appropriately selected in a range between 5 micrometers and 50 micrometers, for example, which depends on material or the like of a metal binding portion, i.e., solder joint portion.

The evaluation process includes an operation for obtaining a correlation between the existence ratio of the crystal grains each having the predetermined size or more/less and the number of temperature cycles applied to the solder joint portion, an operation for obtaining a correlation between the existence ratio of the crystal grains each having the predetermined size or more/less and the rate of crack growth, and an operation for obtaining a corresponding existence ratio of the crystal grains each having the predetermined size or more/less at a time of a designated rate of crack growth that is arbitrarily selected (to be explained later) so as to predict the lifespan of the solder joint portion based on the obtained corresponding existence ratio.

Methods for obtaining the crystal grain size in the solder joint portion are shown in (i) to (v) below.

(i) Electron Backscatter Diffraction System (EBSD Method)

An EBSD detector is connected to a scanning electron microscope (SEM) so as to analyze a diffraction pattern of a crystal generating when an electron beam in the SEM strikes a surface of a specimen and then to determine a crystal orientation in a crystalline material of the specimen on the basis of position information, i.e., orientation data acquired at each measurement point on the specimen. The crystal grain size is observed and measured on the basis of a crystal orientation difference. A size in a longitudinal direction of a crystal grain is measured as a crystal grain size. A range of 2 to 180 degrees, 5 to 180 degrees, 10 to 180 degrees, or 15 to 180 degrees, for example, is defined as the crystal orientation difference.

(ii) Reflection Electron Image Observation (SEM)

This method includes observing the crystal grain based on a change in signal intensity (i.e., channeling contrast) caused by the crystal orientation when an electron beam strikes a surface of a specimen to measure the crystal grain size in the solder joint portion.

(iii) Specimen Observation Using Chemical Etching

This method includes forming a contrast between crystal grains having different crystal orientations from each other by means of etching using caustic solution to thereby achieve a condition for observing the crystal grain to measure the crystal grain size. The caustic solution is made up of, for example, hydrochloric acid system, sulfuric acid system, or miscible system consisting of hydrochloric acid and sulfuric acid. For example, a mass ratio between hydrochloric acid, sulfuric acid, and water all of which constitute the miscible system is (1 to 5):(1 to 10):(85 to 98). Specifically, the mass ratio between hydrochloric acid, sulfuric acid, and water is 2:5:93, for example.

(vi) Specimen Observation Using Dry Etching

According to this method, relatively weak grain boundary portions are mainly etched by means of dry etching using an argon ion beam so that the crystal grains constituting the solder joint portion can be observed to thereby measure the crystal grain size.

(v) Polarization Microscope Observation

According to this method, the crystal grains are observed with the use of polarized nature by which a direction of light is altered depending on a crystal structure to thereby measure the crystal grain size in the solder joint portion.

First Embodiment

Figure 1:
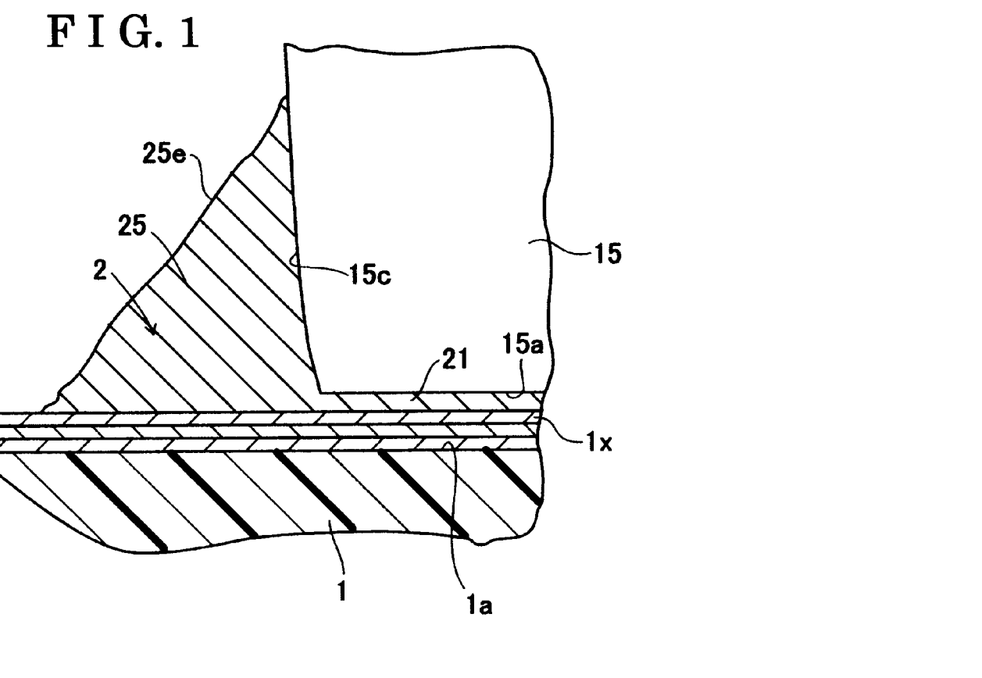
FIG. 1 is a cross-sectional view in the vicinity of a solder joint portion of a board according to a first embodiment of the present invention.

A first embodiment of the present invention will be explained with reference to FIGS. 1 to 7. According to the first embodiment, a board (circuit board) 1 serving as a substrate and of which dimension is 140 mm×70 mm×1.6 mm was prepared as illustrated in FIG. 1. A chip 15 serving as a part (i.e., an electronic part) is joined or mounted to the board 1 by means of a solder joint portion 2 that functions as a metal joint portion. A thin film shaped conduction electrode (i.e., copper electrode) 1x is formed at the board 1. Solder composing the solder joint portion 2 is composed of 3% silver, 0.5% copper in mass ratio, and the remainder including tin and inevitable impurities. However, the composition of the solder joint portion 2 is not limited to the above composition. The solder for the solder joint portion 2 contains substantially no lead (i.e., lead free solder). As illustrated in FIG. 1, the solder joint portion 2 includes a thin solder joint portion 21 having a thin shape and a thick solder joint portion 25 having a thick shape. The thin solder joint portion 21 is arranged between a rear surface 15a of the chip 15 and a front surface 1a of the board 1 so as to function as a solder portion on a lower side of a part (i.e., chip 15, for example). The thick solder joint portion 25 is arranged in contact with a side edge surface 15c of the chip 15 so as to function as a solder portion on a lateral side of a part (i.e., chip 15, for example).

As illustrated in FIG. 1, the thin solder joint portion 21 is sandwiched and supported between the rear surface 15a of the chip 15 and the front surface 1a of the board 1. The thick solder joint portion 25 includes a free end surface 25e. The thick solder joint portion 25 is thicker than the thin solder joint portion 21 and less constrained by the chip 15 and the board 1 than the thin solder joint portion 21. On the other hand, the thin solder joint portion 21 is thinner than the thick solder joint portion 25 and more constrained by the chip 15 and the board 1 than the thick solder joint portion 25.

Next, thermal shock was applied to the aforementioned circuit board 1. Specifically, one temperature cycle (i.e., thermal shock) consists of maintaining the board 1 including the aforementioned solder joint portion 2 at 30° C. (i.e., low temperature atmosphere) for a predetermined time (for example, 30 minutes) and at 80° C. (i.e., high temperature atmosphere) for a predetermined time (for example, 30 minutes) in a temperature cycle test chamber. Then, a temperature cycle process (i.e., thermal shock process) was performed on the board 1 including the solder joint portion 2 to thereby apply thermal shock to the solder joint portion 2 multiple times. In this test, 3,000 temperature cycles were applied to the board 1 according to the present embodiment. The number of temperature cycles is specified as appropriate.

According to the present embodiment, the thin solder joint portion 21 and the thick solder joint portion 25 were separately and individually evaluated in the evaluation process. Specifically, an existence ratio of crystal grains (i.e., tin crystal grains) each having a predetermined size or more (for example, 30 micrometers or more) in the thin solder joint portion 21 was obtained per temperature cycle. The existence ratio of crystal grains each having the predetermined size or more is based on an area fraction thereof in the thin solder joint portion 21. Then, a relationship between the obtained existence ratio and the number of temperature cycles applied to the thin solder joint portion 21 was obtained, which is shown as a correlation diagram A1 in FIG. 2.

Each crystal grain size (precisely, each tin crystal grain size) in the thin solder joint portion 21 was measured on the basis of the EBSD method (Electron Backscatter Diffraction system). At this time, the crystal orientation difference was defined to be 15 degrees to 180 degrees. According to the EBSD method, the tin crystal grains are observed by identifying a crystal orientation difference in solder structure constituting the solder joint portion 2 to thereby obtain the precise tin crystal grain size.

Figure 2:
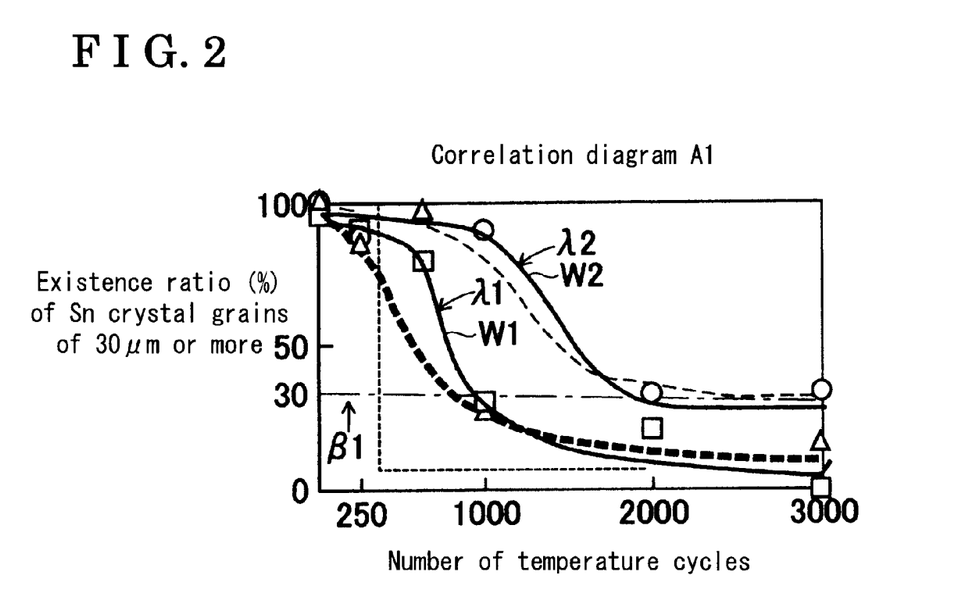
FIG. 2 is a graph illustrating a relationship between an existence ratio of tin crystal grains each having a size equal to or greater than 30 micrometers in a thin solder joint portion and temperature cycles applied to the than solder joint portion according to the first embodiment of the present invention.

In the correlation diagram A1 in FIG. 2, a horizontal axis indicates the number of temperature cycles applied to the thin solder joint portion 21 while a vertical axis indicates the existence ratio (%) of the tin crystal grains each having a size equal to or greater than 30 micrometers in the thin solder joint portion 21. According to the present embodiment, each rectangular mark illustrated in FIGS. 2 to 5 shows a result of a test piece for the solder joint portion 21 having a thickness smaller than 15 micrometers. Each triangular mark illustrated in FIGS. 2 to 5 shows a result of a test piece for the solder joint portion 21 having a thickness from 15 to 30. Each round mark illustrated in FIGS. 2 to 5 shows a result of a test piece for the solder joint portion 21 having a thickness greater than 30 micrometers.

According to the aforementioned correlation diagram A1 in FIG. 2, as shown by a characteristic line W1 for the test piece of which test results are indicated by the rectangular marks and a characteristic line W2 for the test piece of which test results are indicated by the round marks, the tin crystal grain size is gradually reduced when the temperature cycles are repeatedly applied to the solder joint portion 2 of the board 1.

Figure 3:
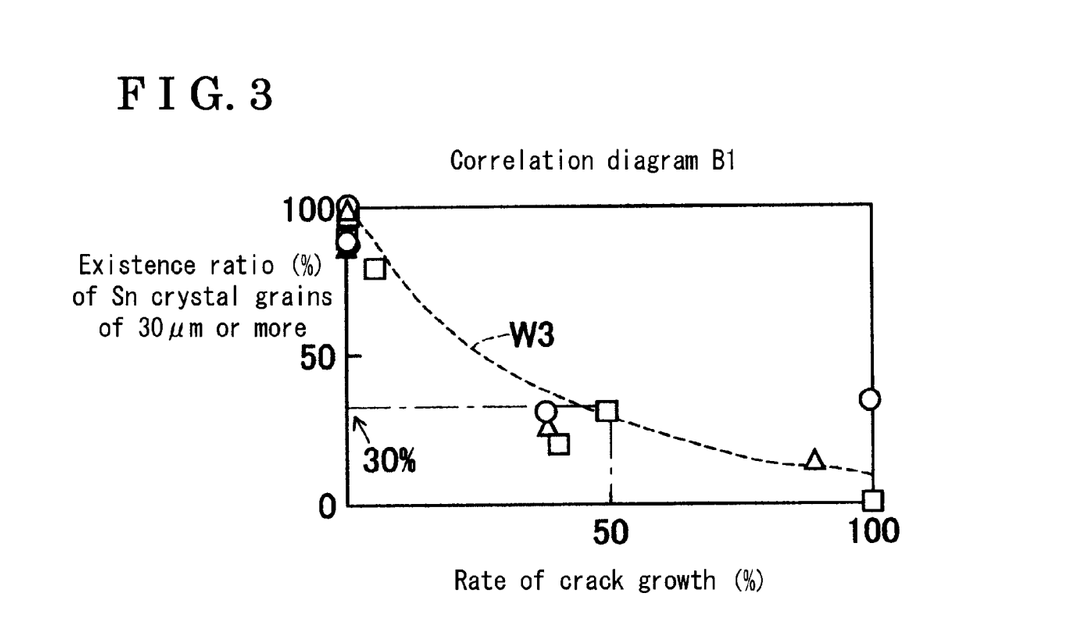
FIG. 3 is graph illustrating a relationship between the existence ratio of tin crystal grains each having a size equal to or greater than 30 micrometers in the thin solder joint portion and a rate of crack growth therein according to the first embodiment of the present invention.

Next, a correlation between the existence ratio (%) of the crystal grains each having a size equal to or greater than 30 micrometers in the thin solder joint portion 21 and the rate of crack growth (%) in the thin solder joint portion 21 was obtained, which is illustrated as a correlation diagram B1 in FIG. 3. In the correlation diagram B1 in FIG. 3, a horizontal axis indicates the rate of crack grown (%) in the thin solder joint portion 21 while a vertical axis indicates the existence ratio (%) of crystal grains each having a size equal to or greater than 30 micrometers. As shown by a characteristic line W3 for the test pieces, when the existence ratio of crystal grains each having a size equal to or greater than 30 micrometers decreases, i.e., the tin crystal grains decrease in size in the thin solder joint portion 21, the rate of crack growth increases and thus it is assumed that the lifespan of the thin solder joint portion 21 is reaching its end.

In order to evaluate the lifespan of the thin solder joint portion 21, the rate of crack growth was arbitrary selected and determined (i.e., designated rate of crack growth). For example, the rate of crack growth was designated to be 50% (i.e., designated rate of crack growth was equal to 50%). In the case of 100% of crack growth, the crack is generated in the entire thin solder joint portion 21. Thus, 50% of crack growth corresponds to a state where the crack is generated in substantially a half of the entire thin solder joint portion 21. According to the correlation diagram B1 illustrated in FIG. 3, the existence ratio (%) of the crystal grains each having a size equal to or greater than 30 micrometers in the thin solder joint portion 21 in the case of the designated rate of crack growth (i.e., 50%) is substantially equal to 30%. Then, an imaginary line β1 indicating 30% of the existence ratio is shown in the correlation diagram A1 in FIG. 2. In an area below the imaginary line β1 in the correlation diagram A1, 50% or more of crack growth is generated in the thin solder joint portion 21. In an area above the imaginary line β1 in the correlation diagram A1, 50% or more of crack growth is prevented from being generated in the thin solder joint portion 21.

According to the correlation diagram A1 in FIG. 2, in the cases where the number of temperature cycles is equal to or smaller than 800, 50% of crack growth is basically not generated in the test pieces of which test results are indicated by the rectangular marks, the triangular marks, and round marks. However, at a time the number of temperature cycles reaches 1,000, the test pieces of which test results are indicated by the rectangular marks and the triangular marks are positioned in the vicinity of the imaginary line β1. That is, 50% of crack growth may occur in such test pieces. Further, according to the correlation diagram A1 in FIG. 2, at a time the number of temperature cycles increases to 2,000, 50% of crack growth tends to occur in the test piece of which test results are indicated by the round marks. In such manner, the possibility of crack growth in the thin solder joint portion 21 is measured.

In the same way, the thick solder joint portion 25 constituting the solder joint portion 2 was tested. Specifically, the existence ratio of crystal grains (i.e., tin crystal grains) each having a predetermined size or more (for example, 30 micrometers or more) in the thick solder joint portion 25 was obtained per temperature cycle. Then, a relationship between the obtained existence ratio and the number of temperature cycles applied to the thick solder joint portion 25 was obtained, which is shown as a correlation diagram A2 in FIG. 4. In the correlation diagram A2 in FIG. 4, a horizontal axis indicates the number of temperature cycles applied to the thick solder joint portion 25 while a vertical axis indicates the existence ratio (%) of the tin crystal grains each having the predetermined size (i.e., 30 micrometers) in the thick solder joint portion 25.

Figure 5:
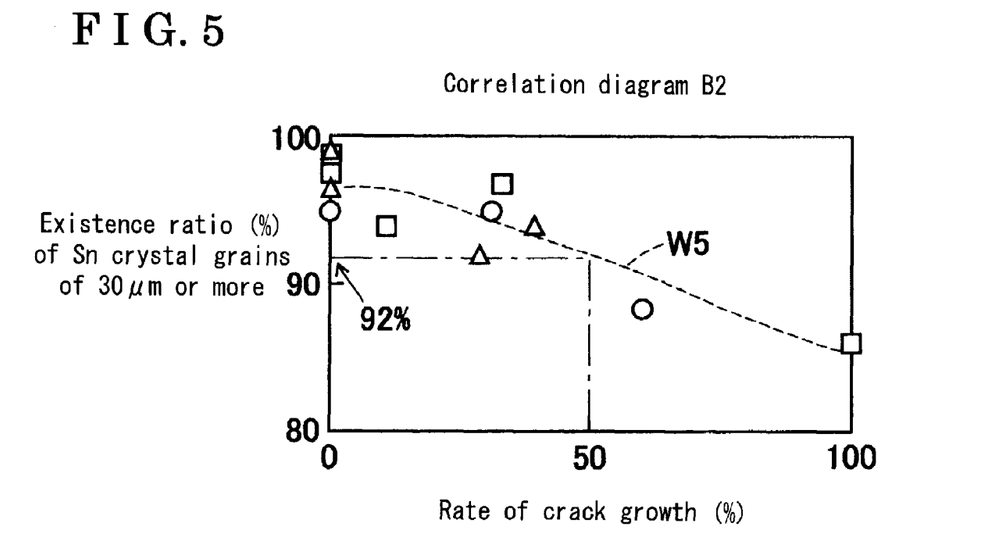
FIG. 5 is a graph illustrating a relationship between the existence ratio of tin crystal grains each having a size equal to or greater than 30 micrometers in the thick solder joint portion and the rate of crack growth therein according to the first embodiment of the present invention.

Next, a correlation between the existence ratio of the crystal grains each having a size equal to or greater than 30 micrometers in the thick solder joint portion 25 and the rate of crack growth in the thick solder joint portion 25 was obtained, which is illustrated as a correlation diagram B2 in FIG. 5. In the correlation diagram B2 in FIG. 5, a horizontal axis indicates the rate of crack grown (%) in the thick solder joint portion 25 while a vertical axis indicates the existence ratio (%) of crystal grains each having a size equal to or greater than 30 micrometers. As indicated by a characteristic line W5 for the test pieces in FIG. 5, when the existence ratio of crystal grains each having a size equal to or greater than 30 micrometers decreases, i.e., the tin crystal grains decrease in size in the thick solder joint portion 25, the rate of crack growth increases and thus it is assumed that the lifespan of the thick solder joint portion 25 is reaching its end.

In order to evaluate the lifespan of the thick solder joint portion 25, the rate of crack growth was arbitrary selected and determined (i.e., designated rate of crack growth). For example, the rate of crack growth was designated to be 50% (i.e., designated rate of crack growth was equal to 50%).

According to the correlation diagram B2 illustrated in FIG. 5, the existence ratio (%) of the crystal grains each having a size equal to or greater than 30 micrometers in the thick solder joint portion 25 in the case of the designated rate of crack growth (i.e., 50%) is substantially equal to 92%. Then, an imaginary line β2 indicating 92% of the existence ratio is shown in the correlation diagram A2 in FIG. 4. In an area below the imaginary line β2 in the correlation diagram A2, 50% or more of crack growth is generated in the thick solder joint portion 25. In an area above the imaginary line β2 in the correlation diagram A2, 50% or more of crack growth is prevented from being generated in the thick solder joint portion 25.

Figure 4:
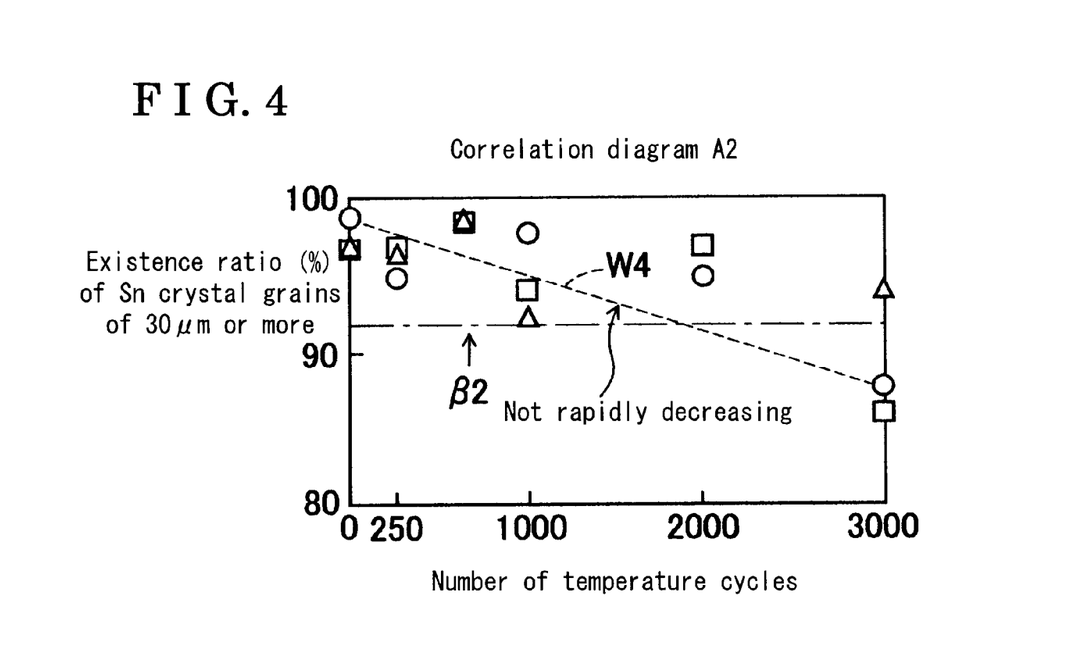
FIG. 4 is a graph illustrating a relationship between the existence ratio of tin crystal grains each having a size equal to or greater than 30 micrometers in a thick solder joint portion and temperature cycles applied to the thick solder joint portion according to the first embodiment of the present invention.

According to the correlation diagram A2 in FIG. 4, in the cases where the number of temperature cycles is equal to or smaller than 2,000, 50% of crack growth is basically not generated in the test pieces of which test results are indicated by the rectangular marks, the triangular marks, and the round marks. However, at a time the number of temperature cycles reaches 3,000, the test pieces of which test results are indicated by the round marks and the rectangular marks are positioned below the imaginary line β2. That is, 50% of crack growth may occur in such test pieces. Further, according to the correlation diagram A2 in FIG. 4, at a time the number of temperature cycles increases to 3,000, 50% of crack growth tends to occur in the test pieces of which test results are indicated by the round marks and the rectangular marks though the crack is not likely to occur in the test piece of which test results are indicated by the triangular marks. In such manner, the possibility of crack growth in the thick solder joint portion 25 and farther the lifespan thereof is measured.

In the case of a comparison between the possibility of crack initiation in the thick solder joint portion 25 and in the thin solder joint portion 21, the crack initiation in the thick solder joint portion 25 is less likely to occur than in the thin solder joint portion 21 with the condition of the same number of temperature cycles. This is because the thin solder joint portion 21 is sandwiched and supported between the board 1 and the chip 15 and thus more constrained thereby than the thick solder joint portion 25. In addition, because of its thin shape, the thin solder joint portion 21 has a difficulty in absorbing shearing strain.

Further, according to the correlation diagram A1 in FIG. 2, the existence ratio (%) of the crystal grains having a size equal to or greater than 30 micrometers tends to decrease when the number of temperature cycles increases. That is, when the number of temperature cycles increases, the tin crystal grain size tends to gradually decrease. Specifically, as shown by the characteristic line W1 for the test piece of which test results are indicated by the rectangular marks in FIG. 2, the existence ratio (%) of the crystal grains having a size equal to or greater than 30 micrometers rapidly decreases when the number of temperature cycles is within a range from 500 to 1,000 (see a sharp drop area λ1). In addition, as shown by the characteristic line W2 for the test piece of which test results are indicated by the round marks in FIG. 2, the existence ratio (%) of the crystal grains having a size equal to or greater than 30 micrometers rapidly decreases when the number of temperature cycles is within a range from 1,000 to 2,000 (see a sharp drop area λ2).

The crack growth in the thin solder joint portion 21 is estimated on the basis of the rapid decrease areas λ1 and λ2 where the crystal grain size decreases rapidly. Further, it is estimated that the lifespan of the thin solder joint portion 21 is reaching its end. In the case of an increase of the crystal grains each of which size is reduced in the thin solder joint portion 21, it can be estimated that the lifespan of the thin solder joint portion 21 constituting the solder joint portion 2 is reaching its end. That is, the lifespan of the solder joint portion 2 is reaching its end in the case of a high rate of the crystal grains each of which size is reduced (i.e., high area fraction) in the solder joint portion 2 upon multiple times of application of the thermal shock to the board 1.

The sharp drop area λ1 and λ2 appear due to the decrease of the tin crystal grain size in the solder joint portion 2 that is caused by the repeated application of the temperature cycles. That is, when the temperature cycles are repeatedly applied to the board 1, the tin crystal grain size is gradually reduced to thereby enhance the possibility of crack growth.

On the other hand, the existence ratio (%) of the crystal grains having a size equal to or greater than 30 micrometers decreases in accordance with the increase of the number of temperature cycles applied to the thick solder joint portion 25, however, the decreasing rate is moderate as shown by the characteristic line W4 in FIG. 4. That is, the existence ratio (%) of the crystal grains having a size equal to or greater than 30 micrometers decreases gently, not rapidly. This is because the thick solder joint portion 25 is not sandwiched or supported by the board 1 and the chip 15 and thus less constrained than the thin solder joint portion 21. In addition, because of its thick shape, the thick solder joint portion 25 can easily absorb the shearing strain. As a result, the existence ratio (%) of the crystal grains having a size equal to or greater than 30 micrometers decreases gently, i.e., the rapid decrease of the tin crystal grain size is not likely to occurs in the thick solder joint portion 25 that functions as the solder portion on the lateral side of the part.

Further, according to the present embodiment, the solder joint portion 2 is divided into multiple areas, i.e., into the thin solder joint portion 21 and the thick solder joint portion 25. Then, the possibility of crack initiation is separately and individually evaluated. Thus, the prediction accuracy of the lifespan of the solder joint portion 2 may be improved.

As mentioned above, the crack is more likely to initiate in the thin solder joint portion 21 than the thick solder joint portion 25. In the cases where the crack initiation and propagation appear in one of the thick solder joint portion 25 and the thin solder joint portion 21, and then the solder joint portion where the crack initiation and propagation appear is split, that split affects the other solder joint portion, in which the crack propagation may then subsequently occur. This is because when the crack initiation and propagation occur in one of the solder joint portions that is then split, the strain caused by the application of temperature cycles may be propagated to the other one of the solder joint portions.

Figure 6:
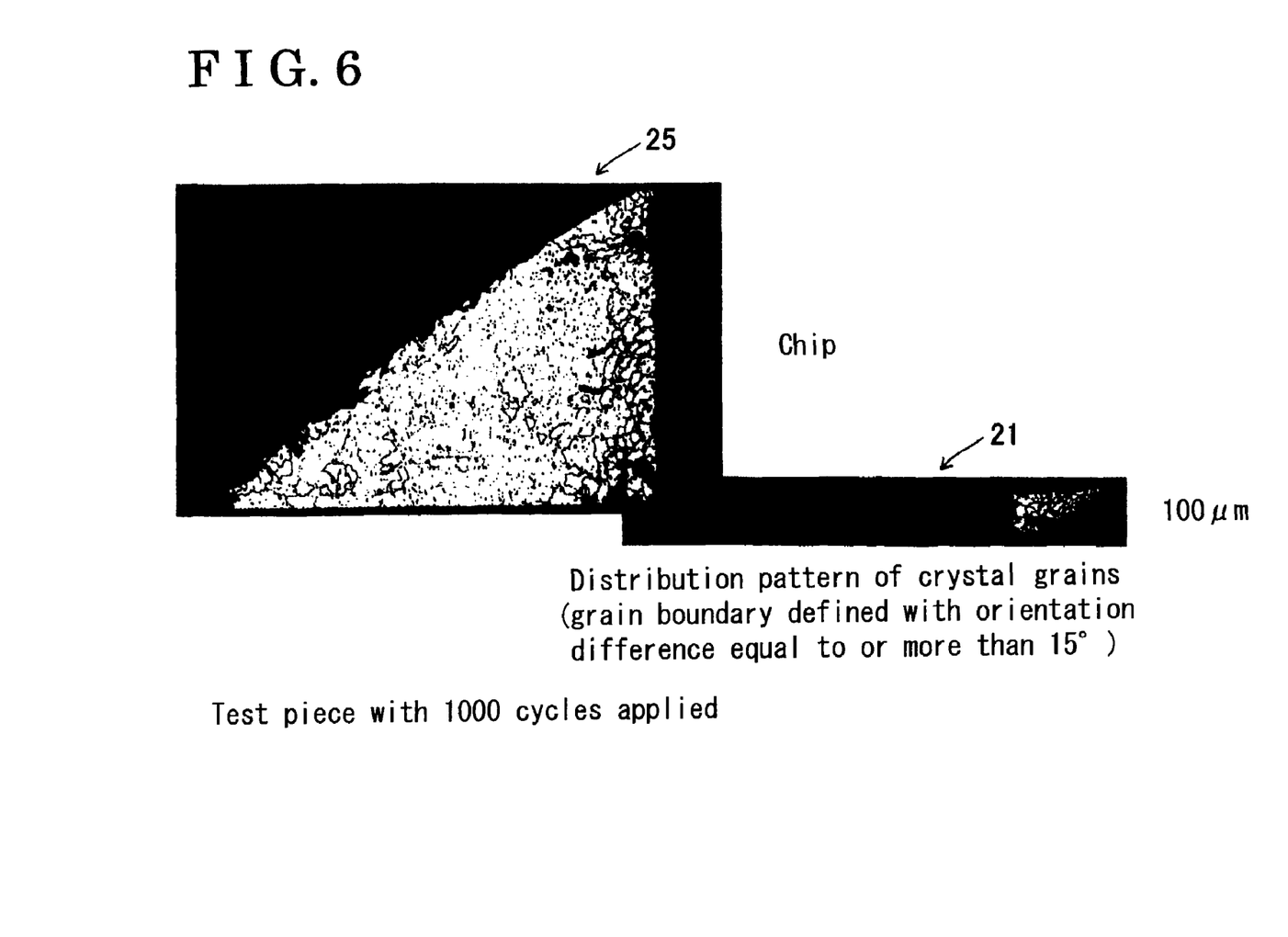
FIG. 6 is an electron microscope picture that captures a structure of the solder joint portion after 1,000 temperature cycles are applied thereto according to the first embodiment of the present invention.
Figure 7A:
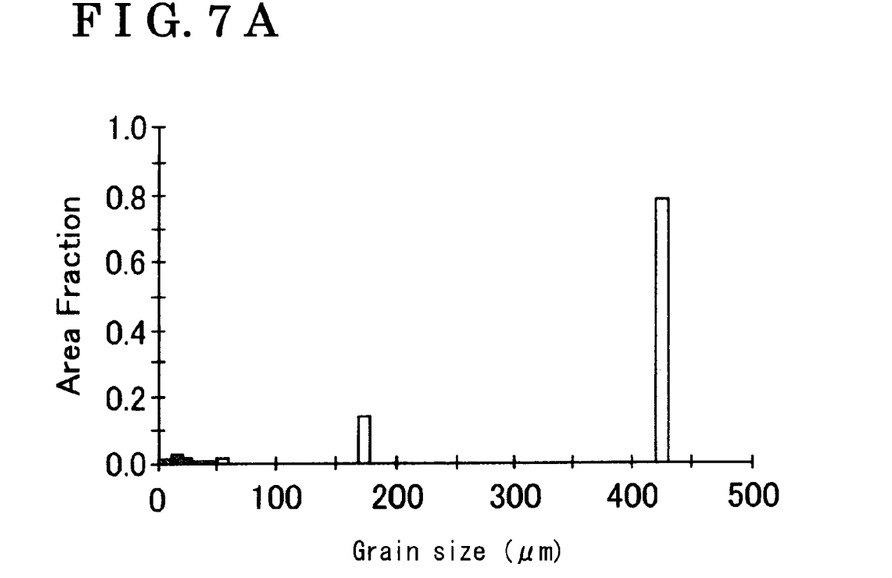
FIG. 7A is a graph illustrating a distribution of crystal grain size in the thick solder joint portion according to the first embodiment of the present invention.
Figure 7B:
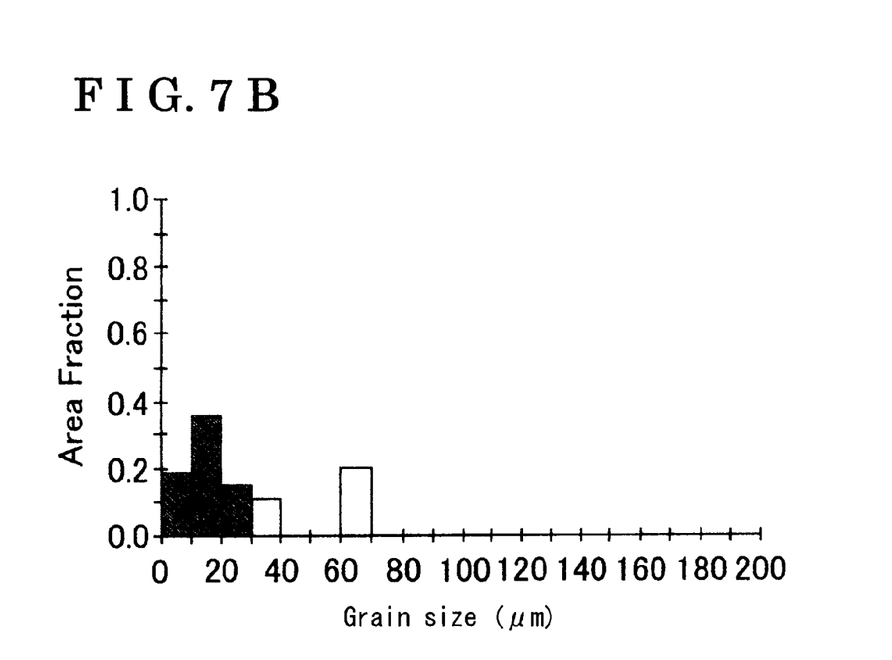
FIG. 7B is a graph illustrating a distribution of crystal grain size in the thin solder joint portion according to the first embodiment of the present invention.

FIG. 6 illustrates a distribution pattern of crystal grains in the cases where a grain boundary is defined with the crystal orientation difference equal to or greater than 15' (precisely, from 15° to 180°). The solder joint portion 2 (i.e., test piece) illustrated in FIG. 6 has been exposed to 1,000 temperature cycles. Hatched areas in FIG. 6 indicate the crystal grains in which grain refining has occurred. FIGS. 7A and 7B each illustrate a distribution of the tin crystal grain size in the test piece illustrated in FIG. 6. Precisely, FIG. 7A is a distribution of the tin crystal grain size in the thick solder joint portion 25 while FIG. 7B is a distribution of the tin crystal grain size in the thin solder joint portion 21. As illustrated in FIG. 7A, the tin crystal grain refining in the thick solder joint portion 25 was prevented from rapidly proceeding even with the application of the temperature cycles. The number of crystal grains each having a size smaller than 30 micrometers were prevented from significantly increasing. On the other hand, as illustrated in FIG. 7B, the tin crystal grain refining in the thin solder joint portion 21 considerably proceeded. The number of crystal grains each having a size smaller than 30 micrometers increased.

Second Embodiment

Figure 8:
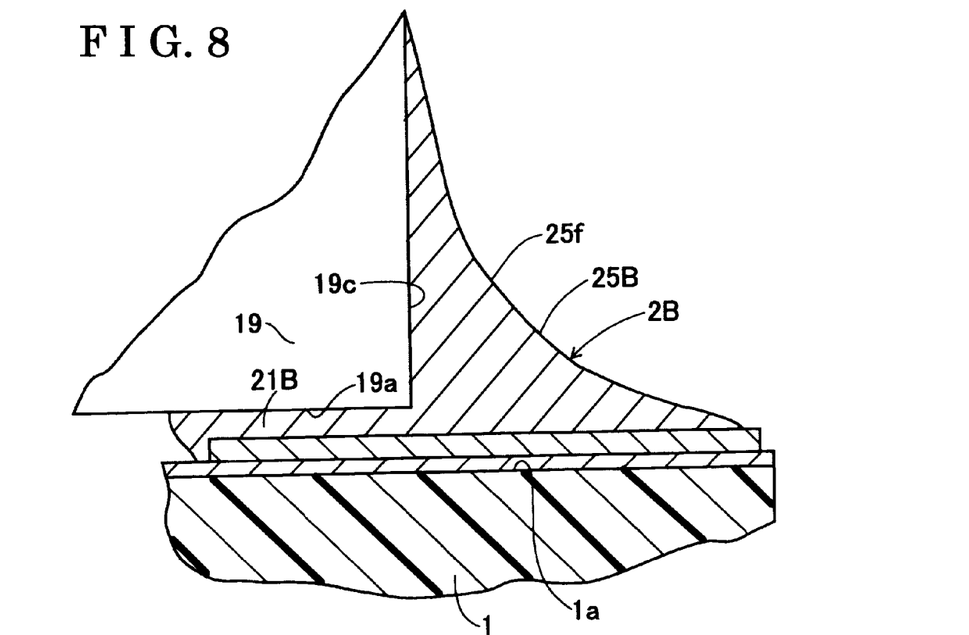
FIG. 8 is a cross-sectional view in the vicinity of a solder joint portion of a board according to a second embodiment of the present invention.

A second embodiment of the present invention will be explained with reference to FIGS. 8 to 13. According to the second embodiment, the board (circuit board) 1 serving as a substrate and of which dimension is 140 mm×70 mm×1.6 mm was prepared as illustrated in FIG. 8. A laminated ceramic capacitor 19 serving as a part (i.e., an electronic part) is joined or mounted to the board 1 by means of a solder joint portion 2B that functions as a metal joint portion.

Solder composing the solder joint portion 2B is composed of 3% silver, 0.5% copper in mass ratio, and the remainder including tin and inevitable impurities. As illustrated in FIG. 8, the solder joint portion 2B includes a thin solder joint portion 21B having a thin shape and a thick solder joint portion 25B having a thick shape. The thin solder joint portion 21B is arranged between a rear surface 19a of the capacitor 19 and the front surface 1a of the board 1 so as to function as a solder portion on a lower side of a part (i.e., laminated ceramic capacitor 19, for example). The thick solder joint portion 25 is arranged in contact with a side edge surface 19c of the capacitor 19 so as to function as a solder portion on a lateral side of a part (i.e., laminated ceramic capacitor 19, for example).

As illustrated in FIG. 8, the thin solder joint portion 21B is sandwiched and supported between the rear surface 19a of the capacitor 19 and the front surface 1a of the board 1. The thick solder joint portion 25B includes a free end surface 25f. The thick solder joint portion 25B is thicker than the thin solder joint portion 21B and less constrained by the capacitor 19 and the board 1 than the thin solder joint portion 21B. On the other hand, the thin solder joint portion 21B is thinner than the thick solder joint portion 25B and more constrained by the capacitor 19 and the board 1 than the thick solder joint portion 25.

Next, thermal shock was applied to the aforementioned solder joint portion 2B of the board 1 in the same way as the first embodiment. That is, the temperature cycle process (i.e., thermal shock process) was performed on the board 1 including the solder joint portion 2B to thereby apply thermal shock to the solder joint portion 2B multiple times. In this test, 3,000 temperature cycles were applied to the board 1 according to the present embodiment.

According to the second embodiment, in the same way as the first embodiment, the thin solder joint portion 21B and the thick solder joint portion 25B were separately and individually evaluated in the evaluation process. Specifically, the existence ratio (%) of crystal grains (i.e., tin crystal grains) each having a size equal to or greater than 30 micrometers in the thin solder joint portion 21B was obtained per temperature cycle. Then, a relationship between the obtained existence ratio and the number of temperature cycles applied to the thin solder joint portion 21B was obtained, which is shown as a correlation diagram A3 in FIG. 9. Each crystal grain size (precisely, each tin crystal grain size) in the thin solder joint portion 21B was measured on the basis of the EBSD method as in the same way as the first embodiment. In this case, the crystal orientation difference was defined to be 15° to 180°.

Each rectangular mark illustrated in FIGS. 9 to 12 shows a result of a test piece for the solder joint portion 21B having a thickness smaller than 15 micrometers. Each triangular mark illustrated in FIGS. 9 to 12 shows a result of a test piece for the solder joint portion 21B having a thickness from 10 to 20 micrometers. Each round mark illustrated in FIGS. 9 to 12 shows a result of a test piece for the solder joint portion 21B having a thickness greater than 20 micrometers.

Figure 9:
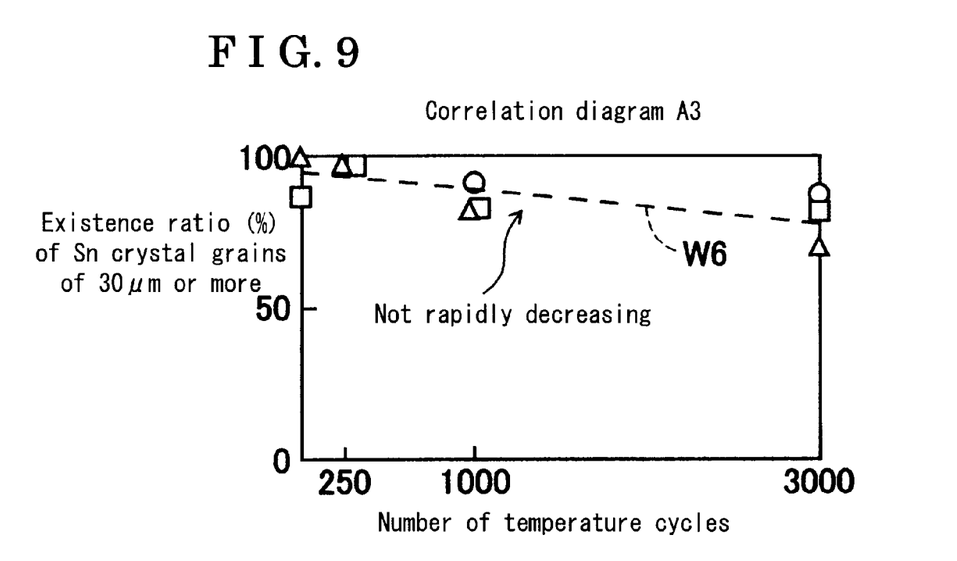
FIG. 9 is a graph illustrating a relationship between an existence ratio of tin crystal grains each having a size equal to or greater than 30 micrometers in a thin solder joint portion and temperature cycles applied to the thin solder joint portion according to the second embodiment of the present invention.

In the aforementioned correlation diagram A3 in FIG. 9, a horizontal axis indicates the number of temperature cycles applied to the thin solder joint portion 21B while a vertical axis indicates the existence ratio (%) of the tin crystal grains each having a size equal to or greater than 30 micrometers in the thin solder joint portion 21B. As shown by a characteristic line W6 for the test pieces in the correlation diagram A3, the tin crystal grain size is gradually reduced when the temperature cycles are repeatedly applied to the solder joint portion 2B of the board 1. However, a sharp drop area where the crystal grain size is rapidly reduced does not appear in the correlation diagram A3. Even when the number of temperature cycles reaches 3,000 cycles, the existence ratio (%) of the tin crystal grains each having a size equal to or greater than 30 micrometers in all the test pieces of which test results are indicated by the rectangular marks, the triangular marks, and the round marks is equal to or greater than 70%. That is, it is unlikely that the tin crystal grain size in all the test pieces for the thin solder joint portion 21B is reduced even when the number of temperature cycles reaches 3,000.

Figure 10:
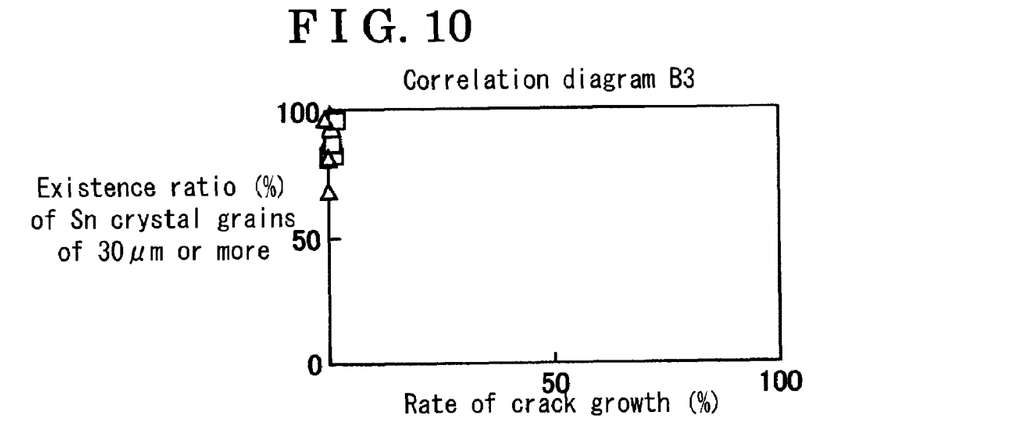
FIG. 10 is graph illustrating a relationship between the existence ratio of tin crystal grains each having a size equal to or greater than 30 micrometers in the thin solder joint portion and a rate of crack growth therein according to the second embodiment of the present invention.
Figure 11:
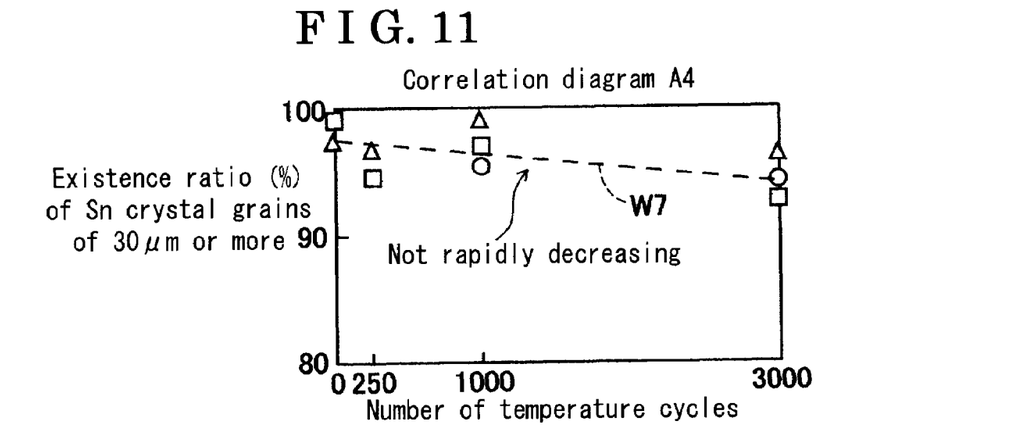
FIG. 11 is a graph illustrating a relationship between the existence ratio of tin crystal grains each having a size equal to or greater than 30 micrometers in a thick solder joint portion and temperature cycles applied to the thick solder joint portion according to the second embodiment of the present invention.

Next, a correlation between the existence ratio of the crystal grains each having a size equal to or greater than 30 micrometers in the thin solder joint portion 21B and the rate of crack growth in the thin solder joint portion 21B was obtained, which is illustrated as a correlation diagram B3 in FIG. 10. In the correlation diagram B3 in FIG. 10, a horizontal axis indicates the rate of crack grown (%) in the thin solder joint portion 21B while a vertical axis indicates the existence ratio (%) of crystal grains each having a size equal to or greater than 30 micrometers.

According to the correlation diagram B3 in FIG. 10, the rate of crack growth of the test pieces of which test results are indicated by the rectangular marks, the triangular marks, and the round marks is substantially zero. That is, it can be estimated that the end point of the lifespan of the thin solder joint portion 21B is far ahead. This estimation can be based on the fact that the crystal grain size in the thin solder joint portion 21B according to the present embodiment is unlikely to become small.

In the same way, the thick solder joint portion 25B constituting the solder joint portion 2B was tested. Specifically, in the evaluation process, a relationship between the existence ratio of crystal grains (i.e., tin crystal grains) each having a size equal to or greater than 30 micrometers in the thick solder joint portion 25B and the number of temperature cycles applied to the thick solder joint portion 25B was obtained, which is shown as a correlation diagram A4 in FIG. 11. In the correlation diagram A4 in FIG. 11, a horizontal axis indicates the number of temperature cycles applied to the thick solder joint portion 25B while a vertical axis indicates the existence ratio (%) of the tin crystal grains each having a size equal to or greater than 30 micrometers in the thick solder joint portion 25B. As shown by a characteristic line W7 for the test pieces in the correlation diagram A4, the crystal grain size is gradually reduced while the temperature cycles are repeatedly applied to the thick solder joint portion 25B. However, a rapid decrease area where the crystal grain size is rapidly reduced does not appear in the correlation diagram A4. Even when the number of temperature cycles reaches 3,000 cycles, the existence ratio of the tin crystal grains each having a size equal to or greater than 30 micrometers in the test pieces of which test results are indicated by the rectangular marks, the triangular marks, and the round marks is equal to or greater than 90%. That is, it is unlikely that the tin crystal grain size in all the test pieces for the thick solder joint portion 25B is reduced even when the number of temperature cycles reaches 3,000.

Figure 12:
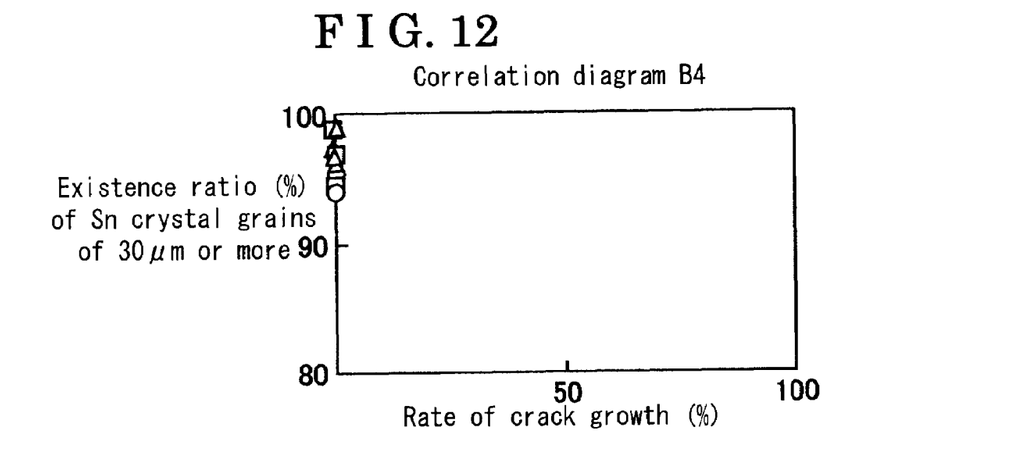
FIG. 12 is graph illustrating a relationship between the existence ratio of tin crystal grains each having a size equal to or greater than 30 micrometers in the thick solder joint portion and the rate of crack growth therein according to the second embodiment of the present invention.

Next, a correlation between the existence ratio of the crystal grains each having a size equal to or greater than 30 micrometers in the thick solder joint portion 25B and the rate of crack growth in the thick solder joint portion 25B was obtained, which is illustrated as a correlation diagram B4 in FIG. 12. In the correlation diagram B4 in FIG. 12, a horizontal axis indicates the rate of crack grown (%) in the thick solder joint portion 25B while a vertical axis indicates the existence ratio (%) of crystal grains each having a size equal to or greater than 30 micrometers. According to the correlation diagram B4, the rate of crack growth of the test pieces of which test results are indicated by the rectangular marks, the triangular marks, and the round marks is substantially zero. That is, it can be estimated that the end point of the lifespan of the thick solder joint portion 25B is far ahead. This estimation can be based on the fact that the crystal grain size in the thick solder joint portion 25B according to the present embodiment is unlikely to become small.

Figure 13:
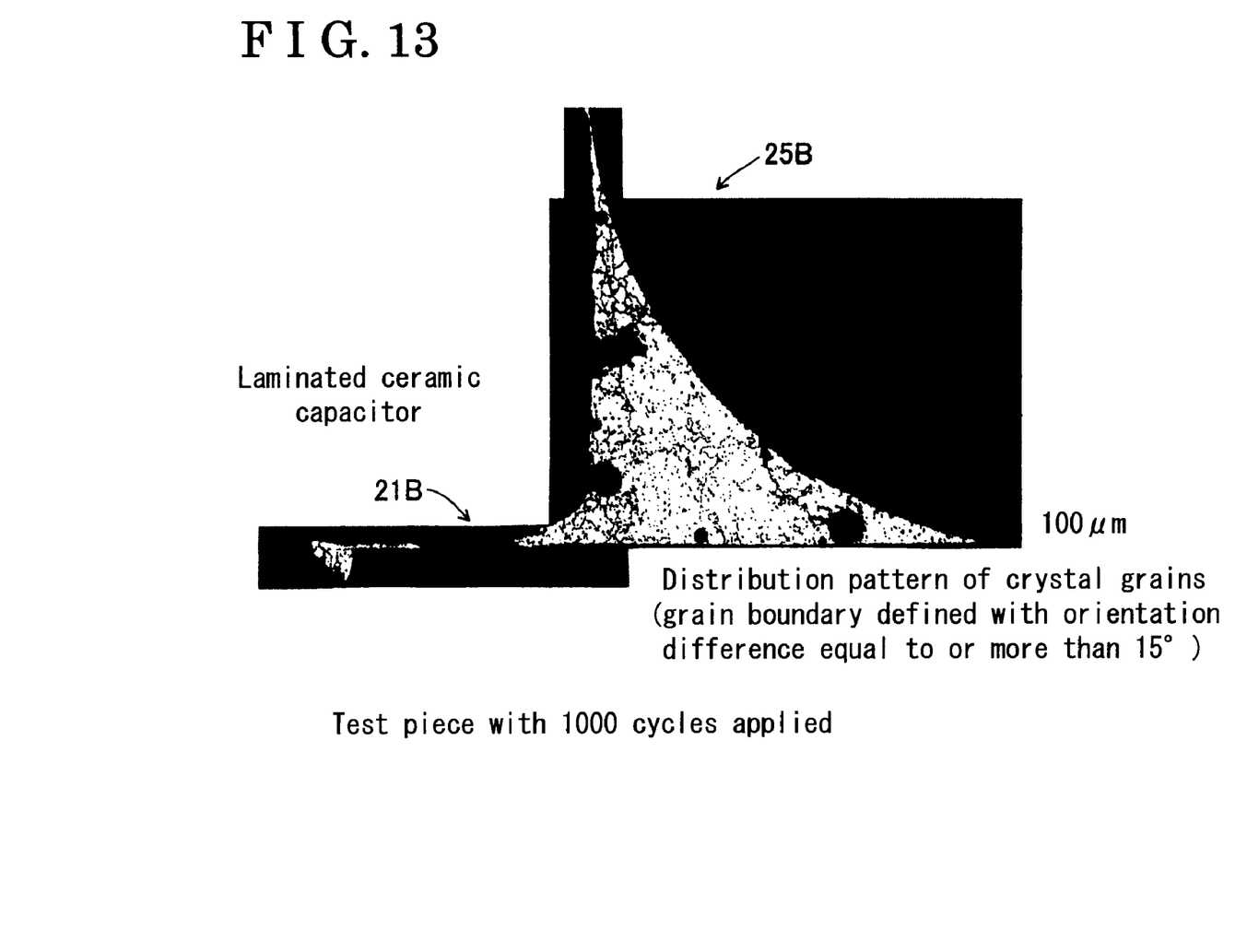
FIG. 13 is an electron microscope picture that captures a structure of the solder joint portion after 1,000 temperature cycles are applied thereto according to the second embodiment of the present invention.

FIG. 13 illustrates a distribution pattern of crystal grains in the cases where a grain boundary is defined with the crystal orientation difference equal to or greater than 15° (precisely, from 15° to 180°). The solder joint portion 2B (i.e., test piece) illustrated in FIG. 13 has been exposed to 1,000 temperature cycles.

According to the aforementioned embodiments, a relationship between the existence ratio of tin crystal grains each having a size equal to or greater than 30 micrometers in the solder joint portion 2 or 2B and the number of temperature cycles applied to the solder joint portion 2 or 2B, and a relationship between the existence ratio of tin crystal grains each having a size equal to or greater than 30 micrometers in the solder joint portion 2 or 2B and the rate of crack growth therein are obtained. Alternatively, the tin crystal grain size used as a basis of the existence ratio (%) may be 10, 20, 40, or 60 micrometers depending on a composition of the solder joint portion 2 or 2B, a type and an intended use of the substrate (i.e., board 1), and the like.

Further, according to the aforementioned embodiments, a relationship between the existence ratio of tin crystal grains each having the predetermined size (i.e., 30 micrometers) or more in the solder joint portion 2 or 2B and the number of temperature cycles applied to the solder joint portion 2 or 2B, and further a relationship between the existence ratio of tin crystal grains each having the predetermined size (i.e., 30 micrometers) or more in the solder joint portion 2 or 2B and the rate of crack growth therein are obtained. Alternatively, a relationship between the existence ratio of tin crystal grains each having the predetermined size (i.e., 30 micrometers) or less in the solder joint portion 2 or 2B and the number of temperature cycles applied to the solder joint portion 2 or 2B, and further a relationship between the existence ratio of tin crystal grains each having the predetermined size (i.e., 30 micrometers) or less in the solder joint portion 2 or 2B and the rate of crack growth therein may be obtained.

Furthermore, according to the aforementioned embodiments, the temperature cycles up to 3,000 are applied to the solder joint portion 2 or 2B. Alternatively, the temperature cycles up to 500, 1000, 5000, 10000, or the like may be applied to the solder joint portion 2 or 2B. The solder composing the solder joint portion 2 or 2B is composed of 3% silver, 0.5% copper in mass ratio, and the remainder including tin and inevitable impurities. Alternatively, the solder in which the tin crystal grain size is changeable in response to the application of the thermal shock such as the temperature cycles may be generally applicable. The dimension of the board 1 is not limited to the aforementioned values and may be defined as appropriate.

The aforementioned embodiments are used for a method for evaluating a solder joint portion. Precisely, the aforementioned embodiments are used for a method for evaluating a solder joint portion attached to an electronic circuit board, an electric circuit board, and the like, or a solder joint portion by means of which non-electric parts are attached.

According to the aforementioned embodiments, the lifespan of the solder joint portion 2 or 2B is evaluated on the basis of the change of the crystal grain size in the solder joint portion 2 or 2B.

Further, according to the aforementioned embodiments, the change of the crystal grain size in the solder joint portion 2 or 2B is based on the initial crystal grain size in the solder joint portion 2 or 2B before the application of the thermal shock and the crystal grain size in the solder joint portion 2 or 2B after the thermal shock is applied multiple times to the solder joint portion. The change of the crystal grain size in the solder joint portion 2 or 2B caused by the application of thermal shock is a measure of the crack growth in the solder joint portion 2 or 2B.

Furthermore, according to the aforementioned embodiments, in the evaluation process, the lifespan of the solder joint portion 2 or 2B is evaluated as reaching an end thereof when the crystal grains each of which size is reduced because of the application of the thermal shock increase.

Furthermore, according to the aforementioned embodiments, in the evaluation process, the change in the existence ratio of crystal grains each having the predetermined size or more before and after the thermal shock process is obtained and the lifespan of the solder joint portion 2 or 2B is evaluated on the basis of the obtained change.

Furthermore, according to the aforementioned embodiments, in the evaluation process, the change in the existence ratio of crystal grains each having the predetermined size or less before and after the thermal shock process is obtained and the lifespan of the solder joint portion 2 or 2B is evaluated on the basis of the obtained change.

Furthermore, according to the aforementioned embodiments, the area in the solder joint portion 2 or 2B where the crystal grain size is first reduced is assumed to be the start point of the crack.

Furthermore, according to the aforementioned embodiments, the crystal grain size in the solder joint portion 2 or 2B is obtained on the basis of the Electron Backscatter Diffraction system.

Furthermore, according to the aforementioned embodiments, the evaluation process includes the operation for obtaining the correlation between the existence ratio of crystal grains each having the predetermined size or more and the number of temperature cycles applied to the solder joint portion 2 or 2B, the operation for obtaining the correlation between the existence ratio of the crystal grains each having the predetermined size or more and the rate of crack growth, and the operation for obtaining the corresponding existence ratio of the crystal grains each having the predetermined size or more at the time of the designated rate of crack growth that is arbitrarily selected so as to predict the lifespan of the solder joint portion 2 or 2B based on the obtained corresponding existence ratio.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. A method of evaluating a solder joint portion by means of which a part and a substrate are joined to each other, the method comprising the steps of:
    preparing the substrate including the solder joint portion;
    applying thermal shock to the solder joint portion multiple times; and
    obtaining the resulting change of a crystal grain size of Sn in the solder joint portion caused by the application of the thermal shock; and
    evaluating a lifespan of the solder joint portion based on the change of the crystal grain size of Sn obtained such that when the existence ratio of crystal grains less than a predetermined value due to the application of thermal shock increases the lifespan of the solder joint portion is deemed to soon expire.

2. A method of evaluating a solder joint portion according to claim 1, wherein the change of the crystal grain size in the solder joint portion is based on an initial crystal grain size in the solder joint portion before the application of the thermal shock and a crystal grain size in the solder joint portion after the thermal shock is applied to the solder joint portion multiple times.

3. A method of evaluating a solder joint portion according to claim 1, wherein during the evaluating, a change in an existence ratio of crystal grains each having a predetermined size or more before and after the thermal shock process is obtained and the lifespan of the solder joint portion is evaluated on a basis of the obtained change.

4. A method of evaluating a solder joint portion according to claim 2, wherein during the evaluating, a change in an existence ratio of crystal grains each having a predetermined size or more before and after the thermal shock process is obtained and the lifespan of the solder joint portion is evaluated on a basis of the obtained change.

5. A method of evaluating a solder joint portion according to claim 1, wherein during the evaluating, a change in an existence ratio of crystal grains each having a predetermined size or less before and after the thermal shock process is obtained and the lifespan of the solder joint portion is evaluated on a basis of the obtained change.

6. A method of evaluating a solder joint portion according to claim 2, wherein during the evaluating, a change in an existence ratio of crystal grains each having a predetermined size or less before and after the thermal shock process is obtained and the lifespan of the solder joint portion is evaluated on a basis of the obtained change.

7. A method of evaluating a solder joint portion according to claim 1, wherein an area in the solder joint portion where the crystal grain size is first reduced is assumed to be a start point of a crack.

8. A method of evaluating a solder joint portion according to claim 1, wherein the crystal grain size in the solder joint portion is obtained on a basis of an Electron Backscatter Diffraction system.

9. A method of evaluating a solder joint portion according to claim 1, wherein the evaluating includes an operation for obtaining a correlation between an existence ratio of crystal grains each having a predetermined size or more and the number of temperature cycles applied to the solder joint portion, an operation for obtaining a correlation between the existence ratio of the crystal grains each having the predetermined size or more and a rate of crack growth, and an operation for obtaining a corresponding existence ratio of the crystal grains each having the predetermined size or more at a time of a designated rate of crack growth that is arbitrarily selected so as to predict the lifespan of the solder joint portion based on the obtained corresponding existence ratio.

10. A method of evaluating a solder joint portion according to claim 1, wherein the evaluating includes an operation for obtaining a correlation between an existence ratio of crystal grains each having a predetermined size or less and the number of temperature cycles applied to the solder joint portion, an operation for obtaining a correlation between the existence ratio of the crystal grains each having the predetermined size or more and a rate of crack growth, and an operation for obtaining a corresponding existence ratio of the crystal grains each having the predetermined size or more at a time of a designated rate of crack growth that is arbitrarily selected so as to predict the lifespan of the solder joint portion based on the obtained corresponding existence ratio.

11. A method of evaluating a solder joint portion according to claim 3, wherein the predetermined size falls within a range between 5 micrometers and 50 micrometers.

12. A method of evaluating a solder joint portion according to claim 9, wherein the predetermined size falls within a range between 5 micrometers and 50 micrometers.

13. A method for evaluating a solder joint which joins a part and a substrate, comprising:
- thermally shocking the solder joint more than once;
- determining the change in the Sn crystal grain size and/or number in the solder joint after the thermal shocking;
- evaluating a lifespan of the solder joint, wherein the evaluating is based on the change of the Sn crystal grain size and/or the ratio of the number of Sn crystal grains of a predetermined size, before and after the thermal shocking; and
- predicting the lifespan of the solder joint based on the change of the Sn crystal grain size and/or the ratio or the number of Sn crystal grains.

* * * * *